`US005772987A`

United States Patent [19]

Hansenne et al.

[11] Patent Number: 5,772,987
[45] Date of Patent: Jun. 30, 1998

[54] PHOTOPROTECTIVE/COSMETIC COMPOSITIONS COMPRISING $TiO_2$ NANOPIGMENTS AND ACYLAMINO ACIDS

[75] Inventors: Isabelle Hansenne, Paris; Alain Lety, Lagny sur Marne, both of France

[73] Assignee: Société l'Oréal S.A., Paris, France

[21] Appl. No.: 725,494

[22] Filed: Oct. 4, 1996

[30] Foreign Application Priority Data

Oct. 4, 1995 [FR] France ................... 95 11662

[51] Int. Cl.⁶ .................. A61K 7/42; A61K 9/10; A61K 31/195; A61K 9/15
[52] U.S. Cl. .............. 424/59; 424/401; 424/450; 424/489
[58] Field of Search ............... 424/401, 450, 424/59, 489

[56] References Cited

U.S. PATENT DOCUMENTS

| | | | |
|---|---|---|---|
| 5,330,758 | 7/1994 | Hansenne-Richoux | 424/450 |
| 5,362,494 | 11/1994 | Zysman | 424/401 |
| 5,449,403 | 9/1995 | Andrean et al. | 102/498 |
| 5,468,471 | 11/1995 | Zecchino et al. | 424/59 |
| 5,468,474 | 11/1995 | Honda et al. | 424/70.1 |
| 5,538,716 | 7/1996 | Forestier | 424/59 |
| 5,556,641 | 9/1996 | Lambridis et al. | 424/490 |
| 5,582,818 | 12/1996 | Nakanishi | 424/59 |
| 5,643,557 | 7/1997 | Eteve et al. | 424/60 |

FOREIGN PATENT DOCUMENTS

| | | |
|---|---|---|
| 0679382 | 11/1995 | European Pat. Off. . |
| 95/12381 | 5/1995 | WIPO . |

OTHER PUBLICATIONS

Gunthert et al. Rev Prog. Coloration vol. 19 pp. 41–49 (1989), Jan. 1989.
STN, Serveur de Bases de Donnees, XP002005227, Karlsruhe, DE, Fichier Chemical Abstracts, vol. 117, nA 50852.
Patent Abstracts of Japan, vol. 13, No. 553 (C–663) [Abstract of JP–A–01 228537] (Ajinomoto Co.).

*Primary Examiner*—Marian C. Knode
*Assistant Examiner*—Mary K. Zeman
*Attorney, Agent, or Firm*—Burns, Doane, Swecker & Mathis, L.L.P.

[57] ABSTRACT

Novel photoprotective/cosmetic photocoloration-resistant compositions, well suited for the photoprotection of human skin and/or hair, comprise an effective UV-screening amount of at least one titanium dioxide nanopigment and an effective photobluing-reducing amount of at least one ionic amphiphilic lipid which comprises an acylamino acid, in a cosmetically acceptable vehicle therefor.

19 Claims, No Drawings

PHOTOPROTECTIVE/COSMETIC COMPOSITIONS COMPRISING TIO₂ NANOPIGMENTS AND ACYLAMINO ACIDS

BACKGROUND OF THE INVENTION

1. Technical Field of the Invention

The present invention relates to novel compositions for topical application, more particularly intended for the photoprotection of the skin and/or hair against ultraviolet radiation, and to cosmetics comprised thereof. More especially, this invention relates to novel, stable color compositions, in a cosmetically acceptable vehicle, comprising at least one titanium dioxide nanopigment and at least one acylamino acid or derivative thereof.

2. Description of the Prior Art

It is known to this art that light radiation having wavelengths of between 280 nm and 400 nm permits tanning of human skin and that radiation having wavelengths of between 280 nm and 320 nm, known as UV-B, causes erythemas and skin burns which adversely affects the development of natural bronzing; this UV-B radiation must therefore be screened.

It is also known to this art that UV-A radiation, having wavelengths of between 320 nm and 400 nm, which causes the skin to tan, effects detrimental changes in the skin, especially in the case of sensitive skin or skin which is continually exposed to solar radiation. In particular, UV-A radiation causes a loss of skin elasticity and the appearance of wrinkles which results in premature aging. It promotes the triggering of the erythemal reaction or accentuates this reaction in certain subjects and can even be the cause of phototoxic or photoallergic reactions. It is therefore desirable to screen the UV-A radiation as well.

Various classes of sunscreening agents are commercially available for screening UV-A and UV-B radiation: inorganic pigments and organic screening agents. These screening agents must be able to absorb or block harmful radiation from the sun while remaining inoffensive to the user.

To this end, metal oxide pigments are increasingly formulated into anti-sun products and day products, in particular makeup products, taking account of their properties of scattering and reflecting UV radiation, which render same highly advantageous in terms of photoprotection: used alone, they provide good protection against UV radiation; in combination with organic screening agents, they permit formulation of highly photoprotective products.

The most widespread inorganic pigment currently used is titanium dioxide, preferably in the nanopigment form, the screening properties of which are well known to this art.

However, compositions containing titanium dioxide pigments are unstable towards light in an oxygen-free medium, which instability is reflected by the appearance of a blue coloration. This photocoloration, known as photobluing, is obviously not desirable from an aesthetic standpoint.

For the purpose of limiting this photoreactivity phenomenon, surface-treated TiO₂ pigments have been provided. Thus, EP-B-0,461,130 describes TiO₂ nanoparticles which have been treated with phosphate anions. Similarly, cosmetics are also available containing of TiO₂ pigments which have been surface-treated with silica or alumina. However, these treatments are expensive and difficult to carry out.

Lastly, while it is true that these surface treatments make it possible to reduce the photoinstability of metal oxide pigments, and in particular the photobluing of substrates containing TiO₂ pigments, this decrease still remains insufficient.

In French Patent Application FR 95/07,001, assigned to the assignee hereof, a solution to the problem indicated above is described, entailing encapsulating metal oxides within lipid vesicles.

A cosmetic composition comprising a microsphere dispersion and at least one metal oxide is described in WO-95/12,381. One example in this '381 application describes a composition which can comprise, inter alia, from 1% to 10% of titanium dioxide and from 0% to 10% of lauroyllysine. However, this example specifies neither the size of the titanium dioxide employed nor any reduction of the photobluing of such titanium dioxide by the lauroyllysine.

Serious need therefore continues to remain for photostable compositions containing titanium dioxide pigments which are devoid of protective vesicles. Consistent herewith, by the term "photostable" is intended that a given composition is not, or is only slightly, subject to the photocoloration phenomenon described above.

SUMMARY OF THE INVENTION

It has now unexpectedly been determined that the formulation, into compositions containing $TiO_2$ pigments, of at least one ionic amphiphilic lipid selected from among the acylamino acids, and in particular from among the acylglutamates, significantly reduces the photobluing phenomenon intrinsically associated with such compositions.

Briefly, the present invention features photoprotective/cosmetic compositions for topical application, in particular for the photoprotection of the skin and/or hair, which do not contain vesicles and which comprise, in a cosmetically acceptable vehicle, at least one titanium oxide nanopigment and at least one ionic amphiphilic lipid selected from among the acylamino acids.

DETAILED DESCRIPTION OF BEST MODE AND SPECIFIC/PREFERRED EMBODIMENTS OF THE INVENTION

More particularly according to the present invention, the ionic amphiphilic lipid is advantageously an acylglutamate.

The compositions of this invention present the advantage of exhibiting very little susceptibility to photobluing.

The compositions according to the invention additionally present the advantage of exhibiting little susceptibility to whitening when they are applied to the skin. Finally, these compositions are very soft and have an excellent sun protection factor.

This invention also features formulating the subject compositions into cosmetics for the protection of the skin and/or hair against ultraviolet radiation, in particular solar radiation.

The present invention, thus, also features a cosmetic treatment for the protection of the skin and/or hair against ultraviolet radiation, in particular solar radiation, which comprises topically applying an effective amount of a composition as described above to the skin and/or hair.

The acylamino acid, preferably an acylglutamate, is formulated into a composition containing titanium dioxide pigments, in order to decrease the photobluing due to the presence of said pigments.

Thus, the photobluing of a cosmetic and/or dermatological composition containing titanium dioxide pigments is reduced via the introduction into said composition of at least one acylamino acid, preferably at least one acylglutamate.

The amphiphilic lipids according to the present invention are ionic amphiphilic lipids selected from among the acylamino acids.

In a preferred embodiment of the invention, the ionic amphiphilic lipid is an acylglutamate and in particular an acylglutamate in which the acyl radical has from 10 to 30 carbon atoms. This radical preferably has from 10 to 20 carbon atoms. In another preferred embodiment of the invention, the acylglutamates are mono- or disodium acylglutamates. Compounds which are particularly well suited for incorporation into the compositions of the present invention are monosodium stearoylglutamate, monosodium myristoylglutamate, monosodium lauroylglutamate and disodium stearoylglutamate, marketed under the trademarks "Acylglutamate HS 11", "Acylglutamate MS 11", "Acylglutamate LS 11" and "Acylglutamate HS 21," respectively, by Ajinomoto.

The acylglutamates are advantageously present in the compositions of the invention in an amount greater than 0.2% by weight with respect to the total weight of the composition and preferably greater than 0.5%.

One of the essential characteristics of the compositions of the present invention is that they contain titanium dioxide nanopigments. By "nanopigments" are intended pigments in which the average size of the elementary particles ranges from 5 to 100 nm. Preferably, the average size of the elementary particles of the nanopigments of the present invention ranges from 10 to 50 nm. Such titanium dioxide nanopigments are common in the cosmetics industry as screening agents and may be treated or untreated.

The titanium dioxide may be in rutile, anatase or amorphous form but is preferably in the rutile and/or anatase form.

The treated nanopigments may, for example, be treated with alumina, silica, aluminum compounds, silicon compounds, sodium compounds, iron oxides, iron esters, stearic acid or glycerol.

More particularly, the treated nanopigments may be titanium oxides treated with:

(1) silica and alumina, such as the products "Microtitanium dioxide MT 500 SA" and "Microtitanium dioxide MT 100 SA" marketed by Tayca, and the products "Tioveil Fin", "Tioveil OP", "Tioveil MOTG" and "Tioveil IPM" marketed by Tioxide, (2) alumina and aluminum stearate, such as the product "Microtitanium dioxide MT 100 T" marketed by Tayca, (3) alumina and aluminum laurate, such as the product "Microtitanium dioxide MT 100 S" marketed by Tayca, (4) iron oxides and iron stearate, such as the product "Microtitanium dioxide MT 100 F" marketed by Tayca, (5) silica, alumina and silicone, such as the products "Microtitanium dioxide MT 100 SAS", "Microtitanium dioxide MT 600 SAS" and "Microtitanium dioxide MT 500 SAS" marketed by Tayca, (6) sodium hexametaphosphate, such as the product "Microtitanium dioxide MT 150 W" marketed by Tayca, (7) octyltrimethoxysilane, such as the product "T-805" marketed by Degussa, (8) alumina and stearic acid, such as the product "UVT-M160" marketed by Kemira, (9) alumina and glycerol, such as the product "UVT-M212" marketed by Kemira,

(10) alumina and silicone, such as the product "UVT-M262" marketed by Kemira.

The untreated titanium dioxides may, for example, be those marketed by Tayca under the trademarks "Microtitanium dioxide MT 500 B" or "Microtitanium dioxide MT 600 B".

The titanium dioxide nanopigment(s) are advantageously present in the compositions according to the invention in an amount ranging from 0.1% to 25% by weight with respect to the total weight of the composition, preferably from 0.2% to 20% by weight with respect to the total weight of the composition.

According to this invention, it is possible, without any problem, to incorporate relatively large amounts of $TiO_2$, in particular amounts greater than 5% by weight, or even greater than 10% by weight, or even greater than 15% by weight, without being or while being only slightly adversely affected by the photobluing phenomenon indicated above.

The sunscreen cosmetic compositions according to the invention can, of course, also contain one or a number of hydrophilic or lipophilic sunscreening agents which are active against UV-A and/or UV-B (absorbers). These screening agents are advantageously selected from among cinnamic derivatives, salicylic derivatives, camphor derivatives, triazine derivatives, benzophenone derivatives, dibenzoylmethane derivatives, β,β-diphenylacrylate derivatives, p-aminobenzoic acid derivatives or the polymer screening agents and silicone screening agents described in WO-93/04,665. Exemplary UV-A screening agents which can be incorporated into the compositions according to the invention include the butylmethoxydibenzoylmethane marketed under the trademark "Parsol 1789" by Givaudan-Roure or the benzene-1,4-di(3-methylidene-10-camphorsulfonic) acid marketed under the trademark "Mexoryl SX" by the assignee hereof. Exemplary UV-B screening agents which are suitable for the compositions according to the invention include 4-methylbenzylidenecamphor or phenylbenzimidazolesulfonic acid marketed under the trademarks "Eusolex 6300" and "Eusolex 232," respectively, by Rona/E. Merck, or 2-ethylhexyl 2-cyano-3,3-diphenylacrylate marketed under the trademark "Uvinul N 539" by BASF. Other examples of organic screening agents are set forth in EP-A-0,487,404.

The compositions according to the invention can also contain agents for the artificial bronzing and/or tanning of the skin (instant tanning agents), such as, for example, dihydroxyacetone (DHA).

The cosmetic compositions according to the invention can also contain pigments or nanopigments other than those indicated above. These pigments can be coated or uncoated metal oxide nanopigments such as, for example, iron oxide, zinc oxide, zirconium oxide or cerium oxide nanopigments, which are all photoprotective agents per se well known as acting by physical blocking (reflection and/or scattering) of the UV radiation. Alumina and/or aluminum stearate are, moreover, conventional coating agents. Such coated or uncoated metal oxide nanopigments are, in particular, described in EP-A-0,518,772 and EP-A-0,518,773.

The compositions of the invention can additionally comprise conventional cosmetic adjuvants and additives, in particular selected from among fatty substances, organic solvents, ionic or non-ionic thickeners, softeners, antioxidants and in particular AFR antioxidants, opacifying agents, stabilizers, emollients, silicones, α-hydroxy acids, anti-foaming agents, moisturizing agents, vitamins, fragrances, preservatives, surface-active agents, fillers, sequestering agents, polymers, propellants, basifying or acidifying agents, dyes, colorants, or any other ingredient commonly formulated into cosmetics, in particular for the manufacture of anti-sun or sunscreen compositions in the form of emulsions.

The fatty substances can comprise an oil or a wax or mixture thereof and they also comprise fatty acids, fatty alcohols and fatty acid esters. The oils are advantageously animal, vegetable, mineral or synthetic oils and in particular liquid petrolatum, liquid paraffin, volatile or non-volatile silicone oils, isoparaffins, poly-α-olefins or fluorinated and perfluorinated oils. The waxes are advantageously animal, fossil, vegetable, mineral or synthetic waxes per se well known to this art.

Lower alcohols and polyols are exemplary organic solvents.

The thickeners are advantageously crosslinked polyacrylic acids, guar gums and celluloses, which may or may not be modified, such as hydroxypropylated guar gum, methylhydroxyethyl cellulose and hydroxypropylmethyl cellulose.

It will of course be appreciated that the optional compound(s) indicated above (screening agents, pigments, adjuvants, and the like) and/or the amounts thereof are selected such that the advantageous properties intrinsically associated with the binary combination according to the invention are not, or not substantially, adversely affected by the envisaged addition(s).

The compositions of the invention can be formulated according to techniques which are well known to this art, in particular for the preparation of emulsions of oil-in-water or water-in-oil type.

The subject compositions are advantageously provided in the form of a simple or complex emulsion (O/W, W/O, O/W/O or W/O/W), such as a cream, a lotion, a milk, a gel or a cream gel, of a powder or of a solid stick and can optionally be packaged as an aerosol and can be provided in the form of a foam or spray.

The cosmetic compositions of the invention are well suited as photoprotective compositions for the human skin or hair against ultraviolet radiation, as anti-sun or sunscreen compositions or as makeup products.

When the cosmetic compositions according to the invention are used for the protection of human skin against UV radiation or as sunscreen compositions, they can be formulated as suspensions or dispersions in solvents or fatty media, or alternatively as emulsions, preferably of oil-in-water type, such as a cream or a milk, or as an ointment, gel, lotion, cream gel, solid stick, stick, aerosol foam or spray.

When the cosmetic compositions according to the invention are used for the protection of hair, they can be formulated as a shampoo, lotion, gel, emulsion or hair lacquer and can comprise, for example, a rinsing composition to be applied before or after shampooing, before or after dyeing or bleaching or before, during or after a permanent-waving or hair-straightening operation, a styling or treating lotion or gel, a lotion or gel for blow drying or setting or a composition for the permanent waving or straightening, dyeing or bleaching of hair.

When the subject compositions are used as makeup products for the eyelashes, eyebrows or skin, such as a skin treatment cream, foundation, lipstick, eye shadow, blusher, mascara or eyeliner, they can be formulated in an anhydrous or aqueous, solid or pasty form, such as oil-in-water or water-in-oil emulsions, or alternatively suspensions.

For example, for anti-sun or sunscreen formulations in accordance with the invention which comprise a vehicle of oil-in-water emulsion type, the aqueous phase (comprising the screening agents or other hydrophilic adjuvants) generally constitutes from 50% to 95% by weight, preferably from 70% to 90% by weight, with respect to the total weight of the formulation, the oily phase (comprising in particular the screening agent(s) and other lipophilic adjuvants) constitutes from 5% to 50% by weight, preferably from 10% to 30% by weight, with respect to the total weight of the formulation, and the (co)emulsifier(s) constitute from 0.5% to 20% by weight, preferably from 2% to 10% by weight, with respect to the total weight of the formulation.

The compositions according to the invention are preferably formulated as an oil-in-water emulsions.

As indicated above, the present invention also features a cosmetic treatment regimen for the skin or hair for photoprotecting same against the adverse effects of UV radiation, comprising topically applying an effective amount of a subject cosmetic composition to the skin or hair.

In order to further illustrate the present invention and the advantages thereof, the following specific examples are given, it being understood that same are intended only as illustrative and in nowise limitative.

EXAMPLE 1

Comparative tests were carried out in order to demonstrate the improvement elicited with respect to photobluing via the incorporation of acylglutamates into a composition containing titanium dioxide nanopigments.

Four oil-in-water emulsions were prepared, each of which containing a certain percentage x of monosodium stearoylglutamate marketed under the trademark "Acylglutamate HS 11" by Ajinomoto and 5% of titanium dioxide marketed under the trademark "MT 100 T" by Tayca. Four emulsions A, B, C and D were thus prepared by varying x from 0% to 5%. The composition of the common vehicle (oil-in-water emulsion) was as follows:

| Vehicle: | |
|---|---|
| (a) Glyceryl mono- and distearate/ polyethylene glycol (100 EO) stearate mixture marketed under the trademark "Arlacel 165" by ICI | 2% |
| (b) Benzoate of $C_{12}/C_{15}$ alcohols marketed under the trademark "Finsolv TN" | 8% |
| (c) Moisturizer | 8% |
| (d) Titanium dioxide marketed under the trademark "MT 100 T" by Tayca | 5% |
| (e) Monosodium stearoylglutamate marketed under the trademark "Acylglutamate HS 11" by Ajinomoto | x % |
| (f) Crosslinked polyacrylic acid marketed under the trademark "Carbopol 980" by Goodrich | 0.3% |
| (g) pH modifying agent | q.s. pH = 7 |
| (h) Preservatives | q.s. |
| (i) Purified water | q.s. for 100% |

For these four compositions, the photobluing was evaluated according to the following procedure: the compositions were introduced into UV-transparent plastic boxes (crystalline polystyrene boxes 50×40×6 cm$^3$) and exposed to UV irradiation (Heraeus Suntest CPS) for 12 hours. Colorimetric measurements were taken using a Minolta CM1000 colorimeter: a first measurement was taken just before exposure to the UV irradiation (T0) and a second after twelve hours of exposure to the UV irradiation (T12h).

The results are expressed in the (L, a, b) system in which L represents the luminance, a represents the red-green axis (−a=green, +a=red) and b represents the yellow-blue axis (−b=blue, +b=yellow).

In order to evaluate the photobluing, the value of interest is ΔE, which measures the variation in total coloration. ΔE is calculated from the variations ΔL, Δa and Δb according to the following formula:

$$\Delta E = \sqrt{(\Delta L)^2 + (\Delta a)^2 + (\Delta b)^2}$$

where:

$\Delta b = b_{T12h} - b_{T0}$ and measures the variation in the blue color, $\Delta L = L_{T12h} - L_{T0}$ and measures the blackening of the composition.

The smaller the value of $\Delta E$, the more effective the protection against photobluing.

The results obtained are reported in Table I below:

TABLE I

| Formula | x % | $\Delta E$ |
|---|---|---|
| A (comparative) | 0 | 32 |
| B (invention) | 0.2 | 27.4 |
| C (invention) | 0.5 | 23.9 |
| D (invention) | 5 | 22.1 |

These results clearly evidence that the incorporation of acylglutamate into compositions containing titanium dioxides significantly decreases the photobluing usually observed with respect to such compositions.

EXAMPLE 2

Three oil-in-water emulsions, E, F and G respectively, were also prepared, each of which containing 1% of acylglutamate and 5% of titanium dioxide marketed under the trademark "MT 100T" by Tayca. The common vehicle for these three emulsions was the same as that employed in Example 1, in which the nature of the acylglutamate was varied. The composition E contained 1% of monosodium myristoylglutamate marketed under the trademark "Acylglutamate MS 11" by Ajinomoto, the composition F contained 1% of monosodium lauroylglutamate marketed under the trademark "Acylglutamate LS 11" by Ajinomoto and the composition G contained 1% of disodium stearoylglutamate marketed under the trademark "Acylglutamate HS 21" by Ajinomoto.

The results, obtained according to the same procedure as for Example 1 above, are reported in Table II below:

TABLE II

| Formula | Acylglutamate | $\Delta E$ |
|---|---|---|
| A (comparative) | no acylglutamate | 32 |
| E (invention) | "Acylglutamate MS 11" | 24.4 |
| F (invention) | "Acylglutamate LS 11" | 24.1 |
| G (invention) | "Acylglutamate HS 21" | 24.6 |

These results clearly evidence that the incorporation of an acylglutamate, whatever its nature, decreases the photobluing related to the presence of titanium dioxide.

EXAMPLE 3

The following oil-in-water emulsion is a specific example of an anti-sun or sunscreen composition in accordance with the invention. The amounts are expressed as % by weight with respect to the total weight of the composition:

| Phase A: | |
|---|---|
| (a) Glyceryl mono- and distearate/ polyethylene glycol (100 EO) stearate mixture marketed under the trademark "Arlacel 165" by ICI | 2% |
| (b) Stearic acid marketed under the trademark "Stéarine TP" by Stéarinerie Dubois | 2.5% |
| (c) Benzoate of $C_{12}/C_{15}$ alcohols marketed under the trademark "Finsolv TN" | 8% |
| (d) Triethanolamine | 0.45% |
| Phase B: | |
| (a') Glycerol | 8% |
| (b') Titanium dioxide marketed under the trademark "MT 100 T" by Tayca | 5% |
| (c') Monosodium stearoylglutamate marketed under the trademark "Acylglutamate HS 11" by Ajinomoto | 0.5% |
| Phase C: | |
| (a") Crosslinked polyacrylic acid marketed under the trademark "Carbopol 980" by Goodrich | 0.3% |
| (b") Cyclopentadimethylsiloxane marketed under the trademark "DC 245 Fluid" | 5% |
| Phase D: | |
| pH modifying agent | q.s. pH = 7 |
| Phase E: | |
| (a''') Preservatives | q.s. |
| (b''') Purified water | q.s. for 100% |

The above composition was formulated in the following manner: the phase A was heated to 80°–85° C. with stirring. The phase B and a portion of the water were then heated to 80°–85° C. with stirring. The phase A was then poured onto the phase B with stirring, in order to produce the emulsion. The mixture was cooled to approximately 45° C. and then the phase C, dispersed in advance, was added. The gel was neutralized. Cooling was continued and the preservatives and the balance of the water were finally added.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A photoprotective cosmetic photocoloration-resistant composition comprising an effective UV-screening amount of at least one titanium dioxide nanopigment and an effective photobluing-reducing amount of at least one ionic amphiphilic lipid comprising an acylamino acid selected from the group consisting of an acylglutamate, monosodium acylglutamate, disodium acylglutamate, monosodium stearoylglutamate monosodium myristoylglutamate, monosodium lauroylglutamate, disodium stearoylglutamate, and acylglutamide, in a cosmetically acceptable vehicle therefor.

2. The photoprotective cosmetic composition as defined by claim 1, wherein said composition is devoid of photoprotecting vesicles.

3. The photoprotective cosmetic composition as defined by claim 1, wherein said at least one ionic amphiphilic lipid comprises an acylglutamate.

4. The photoprotective cosmetic composition as defined by claim 3, wherein the acyl radical of said acylglutamate has from 10 to 30 carbon atoms.

5. The photoprotective cosmetic composition as defined by claim 4, wherein the acyl radical of said acylglutamate has from 10 to 20 carbon atoms.

6. The photoprotective cosmetic composition as defined by claim 1, wherein said at least one ionic amphiphilic lipid comprises a monosodium or disodium acylglutamate.

7. The photoprotective cosmetic composition as defined by claim 6, wherein said at least one ionic amphiphilic lipid comprises monosodium stearoylglutamate, monosodium myristoylglutamate, monosodium lauroylglutamate or disodium stearoylglutamate.

8. The photoprotective cosmetic composition as defined by claim 1, wherein said at least one ionic amphiphilic lipid is at a concentration of greater than 0.2% by weight.

9. The photoprotective cosmetic composition as defined by claim 8, wherein said at least one ionic amphiphilic lipid is at a concentration of greater than 0.5% by weight.

10. The photoprotective cosmetic composition as defined by claim 8, wherein said at least one titanium dioxide nanopigment is at a concentration from about 0.1% to 25% by weight.

11. The photoprotective cosmetic composition as defined by claim 1, wherein said at least one titanium dioxide nanopigment has been treated with alumina, silica, an aluminum compound, a silicon compound, a sodium compound, an iron oxide, an iron ester, stearic acid or glycerol.

12. The photoprotective cosmetic composition as defined by claim 1, further comprising at least one other hydrophilic or lipophilic sunscreen agent.

13. The photoprotective cosmetic composition as defined by claim 1, further comprising at least one other pigment and/or nanopigment.

14. The photoprotective cosmetic composition as defined by claim 1, further comprising at least one cosmetically acceptable additive and/or adjuvant.

15. The photoprotective cosmetic composition as defined by claim 1, comprising an emulsion, cream, lotion, gel, cream gel, milk, powder, solid stick, dispersion, suspension, ointment, shampoo, hair lacquer, rinse, foundation, lipstick, eye shadow, blusher, mascara, eyeliner, paste, aerosol, foam or spray.

16. A method for the photoprotection of human skin and/or hair, comprising topically applying thereto an effective photoprotecting amount of the photoprotective cosmetic composition as defined by claim 1.

17. The composition of claim 1 wherein said acylamino acid is present in an amount greater than 0.2% by weight relative to the total weight of the composition.

18. The composition of claim 17 wherein the amount of said acylamino acid is greater than 0.5% relative to the total weight of the composition.

19. The composition of claim 17 wherein said acylamino acid is an acylglutamide.

* * * * *